United States Patent
Sliwa et al.

(10) Patent No.: US 8,986,292 B2
(45) Date of Patent: Mar. 24, 2015

(54) OPTICAL FEEDBACK RF ABLATOR AND ABLATOR TIP

(75) Inventors: John Sliwa, Los Altos Hills, CA (US); Stephen Morse, Menlo Park, CA (US); Zhenyi Ma, San Jose, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 861 days.

(21) Appl. No.: 13/085,789

(22) Filed: Apr. 13, 2011

(65) Prior Publication Data
US 2012/0265184 A1 Oct. 18, 2012

(51) Int. Cl.
A61B 18/18 (2006.01)
A61B 18/14 (2006.01)
A61B 5/00 (2006.01)
A61B 18/00 (2006.01)

(52) U.S. Cl.
CPC ........... *A61B 18/1492* (2013.01); *A61B 5/0084* (2013.01); *A61B 5/4836* (2013.01); *A61B 5/0086* (2013.01); *A61B 2018/00642* (2013.01); *A61B 2018/00738* (2013.01); *A61B 2018/1472* (2013.01); *A61B 2218/002* (2013.01); *A61B 5/6852* (2013.01); *A61B 5/0075* (2013.01)
USPC ............................................... 606/15; 606/47

(58) Field of Classification Search
USPC .................. 606/7, 13–18, 41–50; 607/88, 89; 600/101
See application file for complete search history.

(56) References Cited

U.S. PATENT DOCUMENTS

| | | | | |
|---|---|---|---|---|
| 7,662,152 | B2 * | 2/2010 | Sharareh et al. | 606/41 |
| 8,500,730 | B2 * | 8/2013 | Lee et al. | 606/41 |
| 2002/0045811 | A1 * | 4/2002 | Kittrell et al. | 600/407 |
| 2007/0287998 | A1 * | 12/2007 | Sharareh et al. | 606/41 |
| 2008/0119694 | A1 * | 5/2008 | Lee | 600/127 |
| 2009/0299354 | A1 * | 12/2009 | Melsky et al. | 606/16 |

OTHER PUBLICATIONS

S.G. Demos, et al., "Real time assessment of RF cardiac tissue ablation with optical spectroscopy", Optics Express, Sep. 12, 2008, 11 pp., vol. 16, No. 19, Optical Society of America, CA, USA.

* cited by examiner

*Primary Examiner* — Ahmed Farah
(74) *Attorney, Agent, or Firm* — Wiley Rein LLP

(57) ABSTRACT

An ablation catheter comprises an elongated catheter body; at least one ablation element disposed in a distal portion which is adjacent the distal end of the catheter body; an illumination optical element disposed in the distal portion, the illumination optical element being light-transmissive to emit light from the illumination optical element to the targeted tissue region; and a collection optical element disposed in the distal portion, the collection optical element being light-transmissive to collect one or more of returned, backscattered or newly excited light from the targeted tissue region. The illumination or excitation optical element and the collection optical element are axially spaced from one another and axially optically isolated from one another within the distal portion to substantially prevent light from traveling between the illumination optical element and the collection optical element along a path within the distal portion.

28 Claims, 7 Drawing Sheets

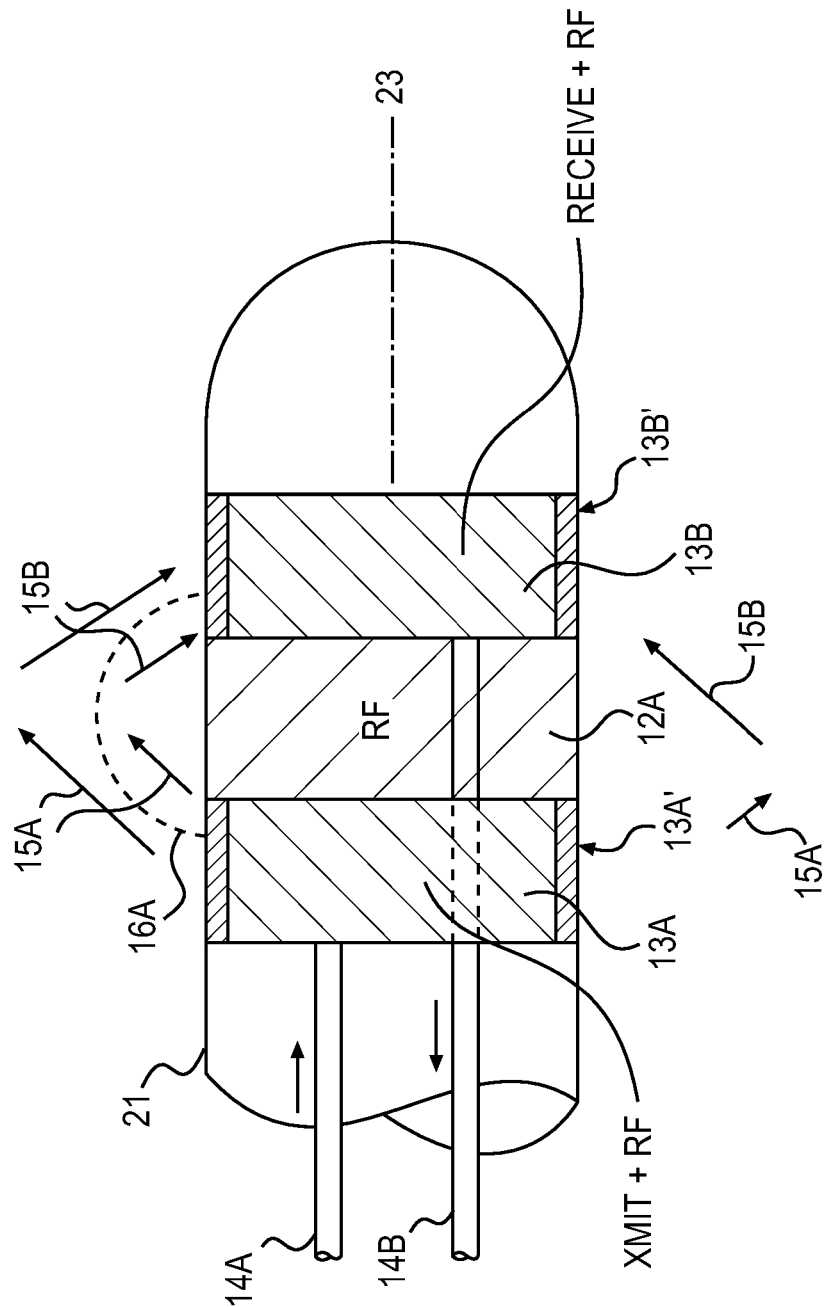

OPTICAL FEEDBACK RF ABLATOR AND ABLATOR TIP

BACKGROUND OF THE INVENTION

The present invention relates generally to ablation devices and, more specifically, to optical feedback radiofrequency (RF) ablators and ablator tips.

Proposed optical-feedback catheters such as those of Biosense-Webster mainly employ an RF catheter in which the thermally ablative RF tip is also capable of the optical detection of the thermal lesions the RF tip forms. See, e.g., US2008/0119694, which is incorporated herein by reference in its entirety. The thermally ablative RF tip has a hollow RF electrode and the outer RF electrode surface is electrically conducting and therefore can deliver RF ablation by electrical contact to target tissue. Inside the hollow metal-coated or metal-walled RF tip electrode are two radially isolated optical elements or chambers, each of which is connected to a separate optical fiber running along the catheter lumen to the proximal catheter handle. The first fiber delivers optically broadband illumination light to the first tip optical cavity (the emission cavity) from which the light emits into nearby tissue through a number of optical vias bridging the tissue and the emission optical element. Thus the emission optical element acts to omni-directionally spray or distribute emanating broadband excitation light from the numerous optical emission vias into the contacting tissue. Note that the omni-directional 360 degree optical output assures that tissue which contacts only one side face of the tip (which is typical) will be illuminated without requiring axial tip rotation. A second optically isolated element in the RF tip is the optical reception element. It is optically coupled to the tissue by a second separate set of interspersed optical vias which receive backscattered light from tissues (i.e., received light which comprises incoming backscattered illumination light). The optical reception element is coupled to the second optical fiber which is used to route incoming backscattered light from the tip back to the catheter handle and to an optical sensor such as an optical spectrometer. The received or backscattered light spectrum is wavelength-scanned by the spectrometer looking for amplitude changes at various wavelengths particularly those corresponding to changing optical absorption or scattering mechanisms in the tissue. Thus, for example, thermal ablation lesions reduce water content in tissue so that optical reflectance or backscattering is affected at one or more wavelengths sensitive to water content. Optical spectroscopy has been used for real time assessment of RF cardiac tissue ablation. See Stavros G. Demos & Shiva Shararch, "Real Time Assessment of RF Cardiac Tissue Ablation with Optical Spectroscopy," Optics Express, Vol. 16, No. 19 (Sep. 15, 2008), which is incorporated herein by reference in its entirety. Note that RF ablations are usually done on target tissue either contacting the side of the RF tip or contacting the end (forward looking end) of the RF tip. Thus most preferably, by omni-directional performance, is meant optical lesion detection of RF lesions both radially (sideways at any rotational angle between 0 and 360 degrees) and forwardly such as with the tip sitting roughly perpendicular to the tissue target or at a tilted angle thereto such as between 0 and 60 degrees.

It has been considered advantageous if not required to optically isolate the two optical elements and their respective sets of optical vias. The argument for this is so as not to saturate the optical receiver (the wavelength spectrometer) with ingoing light which would otherwise travel within the tip directly from the emission fiber to the collection fiber without ever having been emitted from the tip and tissue-scattered. In order to optically isolate the two elements and their respective via sets yet still have omni-directional emanation and reception, the tip is configured to have the emission element within the reception element and it is isolated from it by a radial opaque wall or film. Thus the emission vias, although they pass through the outer reception element, do not dump light directly into the reception element. The reception element vias pass light into the outer annular reception element so that they never penetrate the interior emission element. This arrangement totally isolates the outgoing and incoming optical paths so that reception signal/noise ratio is maximal per such an argument.

A significant drawback of that double walled optical element tip design and interspersed yet isolated optical via sets is that it is very hard to make in terms of difficulty and manufacturing yield and typically requires a double shell structure wherein penetrating optical vias must all be each individually optically isolated. Another problem is that the cumulative area of the emanation optical vias and the cumulative area of the reception optical vias are each quite small; otherwise, the metal shell has too many holes in it to be mechanically sound. The prior art proposed designs such as this also make it difficult to provide a saline irrigated (cooled) RF electrode unless irrigation flow paths double as optical paths. This is considered a limit on the number and scope of possible product designs and not necessarily a technical issue.

BRIEF SUMMARY OF THE INVENTION

In accordance with an aspect of the present invention, an ablation catheter comprises an elongated catheter body extending longitudinally between a proximal end and a distal end along a longitudinal axis; and at least one ablation element disposed in a distal portion which is adjacent the distal end of the catheter body to ablate a targeted tissue region outside the catheter body; an illumination or excitation optical element disposed adjacent the at least one ablation element, the illumination optical element being light-transmissive to emit light from the illumination optical element to the targeted tissue region; and a collection optical element disposed adjacent the at least one ablation element, the collection optical element being light-transmissive to collect one or more of returned, backscattered or newly excited light from the targeted tissue region in response to the light emitted from the illumination or excitation optical element to the targeted tissue region. The illumination or excitation optical element and the collection optical element are axially spaced from one another and axially optically isolated from one another within the distal portion to substantially prevent light from traveling between the illumination optical element and the collection optical element along a path within the distal portion.

In some embodiments, an opaque member is disposed in the catheter body between the illumination optical element and the collection optical element to axially optically isolate the illumination optical element from the collection optical element. The ablation catheter further comprises a first optical fiber in communication with the illumination optical element; and a second optical fiber in communication with the collection optical element. The first optical fiber is optically isolated from the collection optical element and the second optical fiber is optically isolated from the illumination optical element. One or more of the illumination optical element or collection optical element each comprise a substantially annular optical element. The at least one ablation element comprises a metallic shell which at least partially covers the illumination optical element and the collection optical element; and the metallic shell includes a plurality of first openings through which to emit light from the illumination optical element to the targeted tissue region and a plurality of second openings through which to collect, by the collection optical element, light from the targeted tissue region in response to the light emitted from the illumination optical element to the targeted tissue region. The illumination optical element has one or more interior surfaces covered by opaque light-blocking layers; and the collection optical element has one or more interior surfaces covered by opaque light-blocking layers.

In specific embodiments, at least one of the illumination optical elements emits light or the collection elements receives light, along at least one path, oriented at an angle of between about 90 degrees and zero degrees relative to the longitudinal axis. The illumination optical element includes a plurality of illumination optical vias oriented at an angle relative to the longitudinal axis but having a directional component along the longitudinal axis toward the collection optical element; and the collection optical element includes a plurality of collection optical vias oriented at an angle relative to the longitudinal axis but having a directional component along the longitudinal axis toward the illumination optical element. At least one of the illumination or collection optical vias comprises a light conduit for light to travel through, the light conduit including, at least in part, a material selected from the group consisting of liquid, polymer, glass, transparent material, and translucent material. The illumination optical element includes an illumination annular lens to direct light at an angle relative to the longitudinal axis but having a directional component along the longitudinal axis toward the collection optical element; and the collection optical element includes a collection annular lens to receive light at an angle relative to the longitudinal axis but having a directional component along the longitudinal axis toward the illumination optical element.

In some embodiments, the at least one ablation element includes a side-ablating element disposed between the illumination optical element and the collection optical element. The at least one ablation element comprises a first ablation element which is axially situated at an axial distance equal to or greater than zero from the illumination optical element and an axial distance equal to or greater than zero from the collection optical element. An ablation element includes a metal-containing, electrically conductive electrode material. The at least one ablation element includes a forward ablation element disposed at the distal end and adjacent the collection optical element. The forward ablation element comprises a metal-containing solid member having a rounded atraumatic shape. The ablation catheter further comprises a light conduit running axially inside the distal portion, the light conduit for at least one of delivering emitted light to the illumination optical element or receiving returned light from the collection optical element. The ablation catheter further comprises a first optical fiber in communication with the illumination optical element; and a second optical fiber in communication with the collection optical element. The first optical fiber is substantially optically isolated from the collection optical element and the second optical fiber is substantially optically isolated from the illumination optical element. The illumination optical element includes an external illumination annular surface oriented at an angle relative to the longitudinal axis but having a directional component along the longitudinal axis toward the collection optical element; and the collection optical element includes an external collection annular surface having a convex profile, the convex profile including a rearward portion oriented at an angle relative to the longitudinal axis but having a directional component along the longitudinal axis toward the illumination optical element and a forward portion oriented at an angle relative to the longitudinal axis but having a directional component along the longitudinal axis toward the distal light transmission opening.

In specific embodiments, the light transmission element has a hollow interior, and the ablation catheter further comprises at least one irrigation fluid channel coupled with the hollow interior of the light transmission element and being in thermal communication with the distal portion of the catheter body. At least a portion of one of the illumination optical element or the collection optical element is liquid-permeable. The illumination optical element is annular and the collection optical element is annular, and the illumination optical element is axially spaced from the collection optical element. The illumination optical element is coupled to a light source to emit light sideways to the targeted tissue region; and the collection optical element is configured to receive sideways the returned, backscattered or newly excited light from the targeted tissue region in response to the light emitted sideways from the illumination optical element. One element of the illumination optical element or the collection optical element is annular and oriented sideways at an angle relative to the longitudinal axis but having a directional component along the longitudinal axis toward the distal end, and the other element of the illumination optical element or the collection optical element is oriented in a forward direction toward the distal end and disposed distally with respect to the one element.

In accordance with another aspect of the invention, an ablation catheter comprises an elongated catheter body extending longitudinally between a proximal end and a distal end along a longitudinal axis; at least one ablation element disposed in a distal portion which is adjacent the distal end of the catheter body to ablate a targeted tissue region outside the catheter body; an illumination or excitation optical element disposed in the distal portion, the illumination optical element being light-transmissive to emit light from the illumination optical element to the targeted tissue region; and a collection optical element disposed in the distal portion, the collection optical element being light-transmissive to collect one or more of returned, backscattered or newly excited light from the targeted tissue region in response to the light emitted from the illumination or excitation optical element to the targeted tissue region. The illumination or excitation optical element and the collection optical element are axially spaced from one another and axially optically isolated from one another within the distal portion to substantially prevent light from traveling between the illumination optical element and the collection optical element along a path within the distal portion.

In some embodiments, the at least one ablation element is adjacent at least one of the illumination optical element or the collection optical element. The at least one ablation element comprises a metallic film which at least partially covers at least one of the illumination optical element or the collection optical element, the metallic film being substantially transparent optically and electrically conductive. The at least one ablation element further comprises a metal-containing block disposed between the illumination optical element and the collection optical element, the metal-containing block being electrically coupled to the metallic film. The at least one ablation element comprises a metallic shell which at least partially covers at least one of the illumination optical element or the collection optical element; and the metallic shell includes a plurality of first openings through which to emit light from the illumination optical element to the targeted tissue region and a plurality of second openings through which to collect, by the collection optical element, light from the targeted tissue region in response to the light emitted from the illumination optical element to the targeted tissue region. The at least one ablation element comprises a metallic shell which at least partially covers the illumination optical element but not the collection optical element. The at least one ablation element comprises a metal-containing block disposed between the illumination optical element and the collection optical element.

These and other features and advantages of the present invention will become apparent to those of ordinary skill in the art in view of the following detailed description of the specific embodiments.

BRIEF DESCRIPTION OF THE DRAWINGS

FIG. 2C is a sectional view of an optical feedback RF ablator illustrating the use of metallic thin films overlying optical elements.

DETAILED DESCRIPTION OF THE INVENTION

Figure 1A:
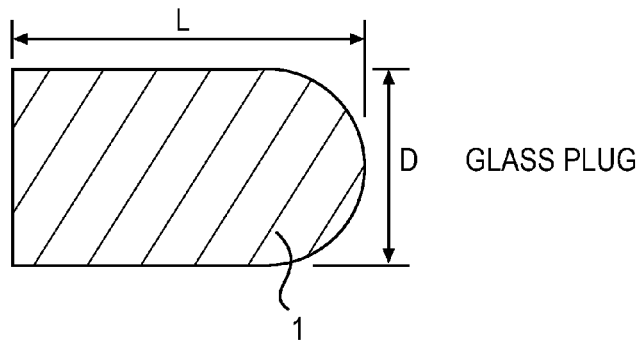
FIGS. 1A-1D are sectional views illustrating a simple method of making a combination RF ablating and optical sensing tip having a single optical tip element for an optical feedback RF ablator which has a metallic shell.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide optical feedback RF ablators and ablator tips.

FIGS. 1A-1D are sectional views illustrating a simple method of making a combination RF ablating and optical sensing tip having a single optical tip chamber or element for an optical feedback RF ablator which has a metallic shell. The same optical element carries emission and reception light; whether that emission and reception is done simultaneously or sequentially depends on the inventive embodiment.

FIG. 1A shows a plug 1 which may be a hot-pressed moldable glass plug of diameter D and length L. The plug 1 has a dome-shaped end and an otherwise cylindrical body in the embodiment shown. The glass in the glass plug 1 is substantially transmissive of the optical wavelengths of interest. Typically these wavelengths at least include some infrared wavelengths to garner maximal tissue penetration. The plug 1 is finish-molded or hot-pressed to final dimension and surface finish as it can be such as by using Sumitomo® moldable lens glass materials in a polished mold. This is referred to as a standalone plug component. As used herein, a plug or a tip plug is a member to be placed in or formed inside of an RF ablating shell whose function is to route light and irrigation fluid (e.g. saline) including being capable of mating to light fibers or conduits and fluid delivery lumens as necessary. The plug material will preferably, at least in some plug portions, be inherently light-transmissive (i.e., such as clear and transparent, translucent, or diffusely transmissive and scattering). Inherently optically transmissive materials include glasses and polymeric materials, both in solid and porous or permeable form. The porosity or permeability, if present, may be saline or liquid/gel saturated during use and might serve as one or both of saline or cooling flow paths and/or localized optical conduits.

Figure 1B:
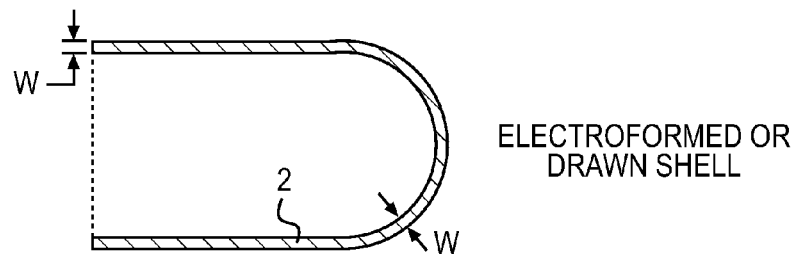

FIG. 1B shows an RF power delivering metallic shell 2 of thickness W. This thickness W is measured in mils or thousandths of an inch such as about 0.001 inches to about 0.025 inches, more preferably about 0.003 inches to about 0.015 inches, most preferably about 0.007 to about 0.012 inches. This metallic or metal-containing shell 2 may be, for example, made via deep drawing metal or by metal electroforming onto a mandrel. The purpose of the shell 2 is to provide most or all of the electrical and thermal conductivity needed by such an RF ablative tip as well as to provide a metallic tip with familiar tissue electrical-contact or electrical work-function properties. In a first specific embodiment, the shell 2 is copper-containing or copper-alloy containing, deep drawn to shape, and over plated/coated with a bilayer such as gold on nickel or platinum on chrome. In a second embodiment the shell 2 is formed by electroforming a metallic shell 2 out of electrodeposited copper or nickel directly onto the glass or polymer plug 1. In that case the glass or polymer plug 1 acts as the electroforming mandrel. As before an overcoat of noble metal such as widely employed platinum or platinum-iridium (or possibly gold or rhodium) could be plated or deposited thereon with an underlying adhesion metal. The construction of the plug 1 and shell 2 forming the tip must assure that during thermal cycling caused by RF ablation differential, thermal expansion of the shell and plug does not cause the plug-shell interface bond to fail in tension or shear. Thus if a low expansion glass plug is used, one may want to use electroformed nickel or deep-drawn Invar® or other low expansion metal for the tip shell with an accompanying noble metal overcoat. If an optical epoxy or polymer is used for the plug material which typically has high thermal expansion, then it is preferably paired with a high expansion shell material such as electroformed copper or a deep-drawn copper alloy. As used herein, a shell or a tip shell is formed of an electrically and thermally conducting metal, metal alloy, metal laminate, metal composite, metal impregnated ceramic, metal impregnated glass, or cermet, either as a standalone component or as a built-up deposit on a mandrel or form, the mandrel or form possibly being disposed of as a disposable after use or being the permanent tip plug. We also note that in the case of a polymeric or epoxy plug, an electroformed or deep-drawn shell can serve as a casting mold for such a cast plug polymer.

Figure 1C:
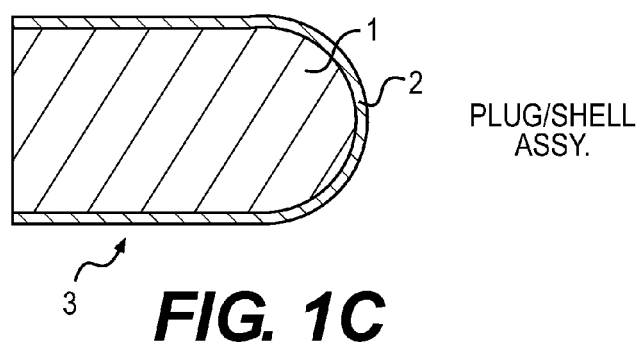

FIG. 1C shows the glass plug 1 and the metallic shell 2 assembled into a subassembly 3. There are various available methods including a number of preferred methods of forming the subassembly 3. According to one method, a preformed standalone plug 1 is epoxy-bonded or cemented into the shell 2 using an optically clear epoxy with an index of refraction allowing for good transmission of the outgoing and ingoing light. In another approach, a plug 1 is thermally molded or cast into the metal shell 2 (using the shell as a casting container or mold), preferably such that an optically transparent bonded plug/shell interface is obtained. In yet another method, the shell 2 is electroformed or plated directly upon a glass or polymeric preformed plug 1. We note that electroforming is actually a form of high-rate plating wherein very thick (mils or more) platings (structural deposits) are desired.

Figures 1, 1D:
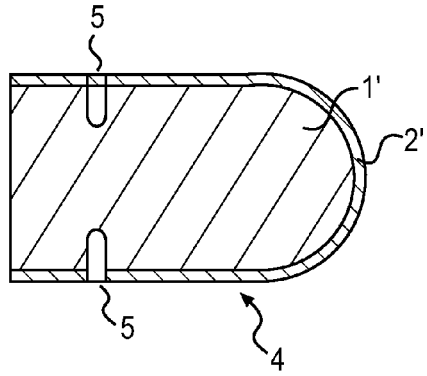

FIG. 1D1 shows a subassembly 4 which is similar to that of FIG. 1C but the subassembly 4 further includes a pair of laser-drilled optical vias 5 through the metal shell 2' and into the underlying plug 1'. It should be noted that after laser-drilling, one may backfill the laser holes with an optical epoxy or with reflowed plug glass. In that manner there is excellent optical coupling from the tissue all the way some distance into the plug 1' along the drilled and filled optical conduit. Furthermore, the optical vias 5 may be arranged to emit light and/or to gather returned or backscattered light. For this embodiment, the plug can be formed by casting or molding it into a shell that already has the optical vias formed therein, and the plug casting or molding process will serve also to fill the shell portion of the vias with the cast or molded optically transmissive material if it is desired to fill the vias. In specific embodiments, multiple optical vias are distributed about the tip surface (around the longitudinal axis of the catheter tip) such that substantially 360 degree radial omni-directional sensing of lesions is rendered possible. Preferably, forward-looking optical vias (not shown in FIG. 1) are also utilized such that tip-end lesions can be monitored as well as tip-side lesions.

Figures 1, 1D, 2:
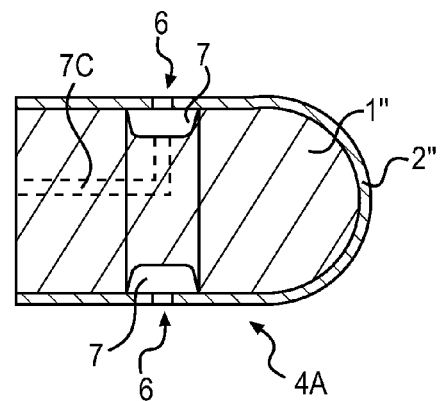

FIG. 1D2 shows a subassembly 4A which again is similar to that of FIG. 1C, but the subassembly 4A further includes an annular cavity 7 formed in the glass or polymeric plug 1". FIG. 1D2 also depicts optical vias 6 in the shell 2" which also fluidicly couple the annular saline chamber or channel 7 with the exterior which may be outside adjacent tissue. It is anticipated that the annular channel 7 will be used to route irrigation fluid such as saline to the ablation tip and out of the ablation tip. FIG. 1D2 shows an irrigation fluid channel 7C coupled with the annular channel 7 (if the plug 1" is liquid-permeable, there may not be a need for a localized irrigation flow channel). For simplicity, irrigation fluid channels are not shown in all the figures, but it is understood that the ablation tips in this disclosure can include any suitable irrigation fluid channel(s) for routing irrigation fluid to various parts of the ablation tips. The irrigation fluid will, as seen in FIG. 1D2, fill the annular chamber 7 and optical vias 6 thereby allowing for uninterrupted light passage along that path. The irrigation fluid will keep the ablation tip cool during ablation (i.e., less that about 70° C.). In this approach, the irrigation fluid such as saline or water acts as an optical waveguide as well as a tip coolant. If the optical via is longer than its lateral dimension (e.g., length greater than diameter) and is filled with an irrigation fluid such as water or saline or an optically transmissive polymer, the filled via physically acts as its own light pipe along its length. In specific embodiments, the plug includes at least one channel or conduit formed on its surface or in its body, which serves to do at least one of the following: couple to an optical fiber, couple to a fluid lumen, pass irrigation fluid through or across any portion of the ablation tip, and pass light or optical energy through or along any portion of the tip regardless of whether the channel is filled with one or more of an irrigation fluid, a light conducting material such as optical epoxy or air, for example.

In the case of a product or device having only one tip-connected fiber (fiber(s) not shown in FIGS. 1A-1D), it will be apparent that in order to have a working device, there is a need to (1) transmit and receive light simultaneously to and from the tip along the single fiber, or (2) transmit and receive light sequentially to and from the tip along the single fiber. We emphasize that by single tip-connected fiber we mean that only a single fiber is routed all the way to the ablation tip. This arrangement does not at all preclude a design utilizing a bifurcated fiber, i.e., a Y-shaped fiber (single fiber which splits into two fibers) wherein the single combined transmit/receive end is in the ablation tip and the dual but separate transmit and receive split ends are respectively away from the tip such as in the device handle. The following discussion addresses these two alternatives for such single fiber-connected tip devices.

Figure 2A:
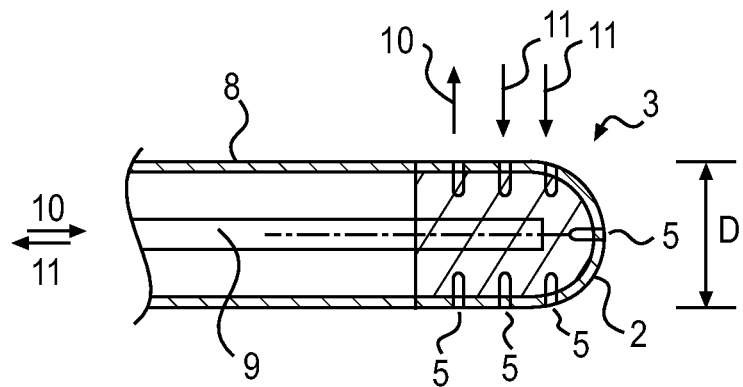
FIG. 2A is a sectional view of an optical feedback RF ablator illustrating a time-gated pitch-catch approach wherein emitted light is pulsed and turned off before received light is collected.

FIG. 2A is a sectional view of an optical feedback RF ablator tip illustrating an RF ablation tip having a single optical tip fiber. Note that the tip-interior region defined by the plug comprises a single optical chamber.

Figure 2B:
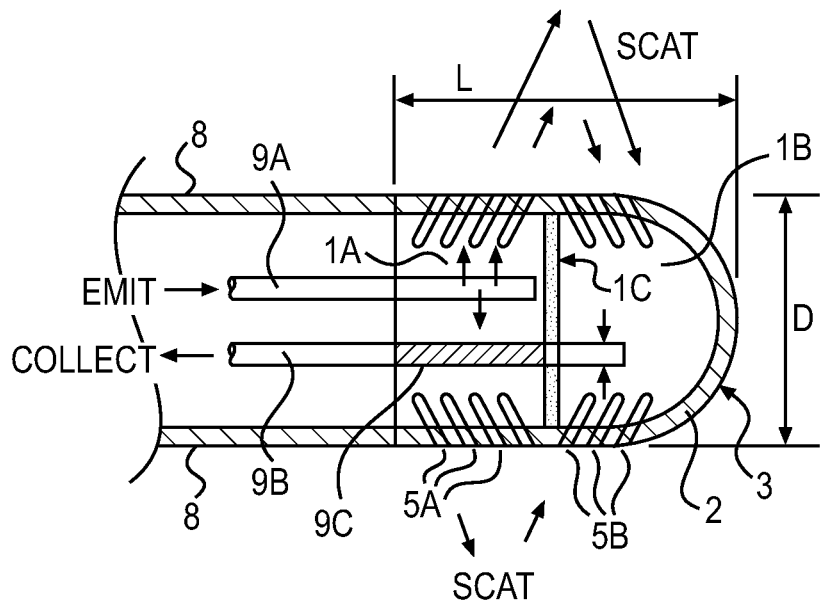
FIG. 2B is a sectional view of an optical feedback RF ablator illustrating a two fiber two optical-element scenario using constant illumination.

FIG. 2B is a sectional view of an optical feedback RF ablator tip illustrating an RF ablation tip having separate tip transmit and receive fibers (two fibers). Note that the tip-interior region defined by the plug comprises two optically isolated chamber regions. While the optical isolation is ideally 100%, it is typically a substantial optical isolation of, for example, preferably at least about 90%, more preferably at least about 99%, and most preferably about 100%.

In the single fiber RF tip of FIG. 2A, a catheter body 8 is connected to the RF tip assembly 3. The catheter body 8 routes an optical fiber 9 to the distal tip 3 from the proximal catheter control handle (not shown). The tip of FIG. 2A shows multiple optical vias or ports 5 laser drilled through the metallic tip shell into the tip interior glass plug or polymer/epoxy plug. The plastic or glass optical fiber 9 is also optically coupled into the tip glass/polymer/epoxy plug. Because the ablator has only one optical fiber 9 within the tip, fiber 9 will serve both to emanate light 10 from the tip and to receive backscattered (or excited fluorescent) light 11 from the tissue regardless of whether one attempts to emit and collect light simultaneously or sequentially.

For clarity we define "simultaneous transmit and receive" to mean that at at least one given instant there is both rightward moving emission and leftward moving received backscattered light in the fiber(s) and that the leftward moving received backscattered light is used to monitor the tissue target or lesion. By the same token by "sequential transmit and receive" we mean that at at least one given instant only leftwards backscattered received light is moving in the fiber(s), wherein the leftwards received light was created by previously rightward moving emission light which was previously backscattered from target tissue. For either arrangement above the returning or leftwards moving light will contain tissue-backscattered light and possibly some undesirable reflective light from inside the tip shell 2 itself. The structure of FIG. 2A is more prone to having some undesired tip-interior reflections since some light emitted from fiber 9 can reflect off the shell 2 interior and go directly back into fiber 9 as "received" light. Such tip-internal reflections reduce the signal/noise ratio for the tissue-reflected light of interest. A way to minimize such tip-interior reflected light in the structure of FIG. 2A is to blacken the interior of the metal shell 2 or the plug/shell interface region or provide the shell's internal surface with an antireflection coating (not shown), for example. In the structure of FIG. 2B, we have optically isolated transmit and receive chambers 1a, 1b and their related fibers 9a,b thus outgoing light from transmit fiber 9a, even if some of it reflects from the shell 2 interior, does not get dumped into the receive fiber 9b. Note that in the structure of FIG. 2B where the collection or receiving fiber 9b passes through the transmission chamber 1a, one needs to provide an opaque coating 9c to prevent dumping of outgoing light directly into the receive path. This opaque fiber coating 9c is in addition to the opaque barrier 1c separating chambers 1a and 1b. It is noted that the opaque barrier 1c is configured to substantially prevent light from traveling directly between the illumination optical element and the collection optical element on the order of preferably at least about 90%, more preferably at least about 99%, and most preferably about 100%. The opaque barrier 1c may be a very thin film, a thin disk, or even a metal-containing ablation member, etc.

For either of the structures of FIG. 2A and FIG. 2B, one can practice simultaneous or sequential emission/reception. A light source for simultaneous emission/reception simply needs to be "on" long enough that for a given instant one has both outgoing rightwards and incoming leftwards returning backscattered light in the single fiber device of FIG. 2A or has rightwards light in fiber 9a and leftwards light in fiber 9b of the dual fiber device of FIG. 2B. By the same token either of the structures of FIG. 2A and FIG. 2B can practice sequential emission/reception such as for FIG. 2A wherein one would first have rightward emittable light and then, afterwards, leftward backscattered light in fiber 9, and for FIG. 2B wherein one would have first rightward emittable light in fiber 9a and then, afterwards, leftwards backscattered light in fiber 9b. This sequential operation would require extremely short light emission pulses.

FIG. 2C is a sectional view of an optical feedback RF ablator illustrating the use of metallic thin films overlying optical elements. In the ablator of FIG. 2B, the optical transmitter 1a and receiver 1b are contained within a metallic RF ablation shell 3 which has optical ports or vias 5a, 5b through which optical light passes outwards and inwards. In other words, the tip-surface real estate is shared between RF ablation and optical transmit/receive functions.

In FIG. 2C, the optical transmitter 13a and receiver 13b have overlying thin films 13a' and 13b' of optically transparent yet electrically conducting metallic film instead of an overlying shell of the RF ablating metal electrode 3 in FIGS. 2A and 2B. This again allows real-estate sharing between ablation and optical transmit/receive functions. An example of suitable metallic films 13a, 13b would be ITO or indium tin oxide widely used in the display industry. FIG. 2C also shows a bulk, substantially solid, intermediate metallic RF ablator member or portion 12a. The ablator member 12a also serves to provide the RF excitation to the transparent electrodes 13a' and 13b' thereby making those optical elements also RF ablator members or portions. The thin film electrodes 13a', 13b' are preferably less than about 3000 angstroms in thickness, more preferably less than about 2000 angstroms in thickness, and most preferably less than about 1200 angstroms in thickness. They are substantially transparent optically, with a transparency of preferably at least about 90%, more preferably at least about 95%, and most preferably about 100%.

Figure 2D:
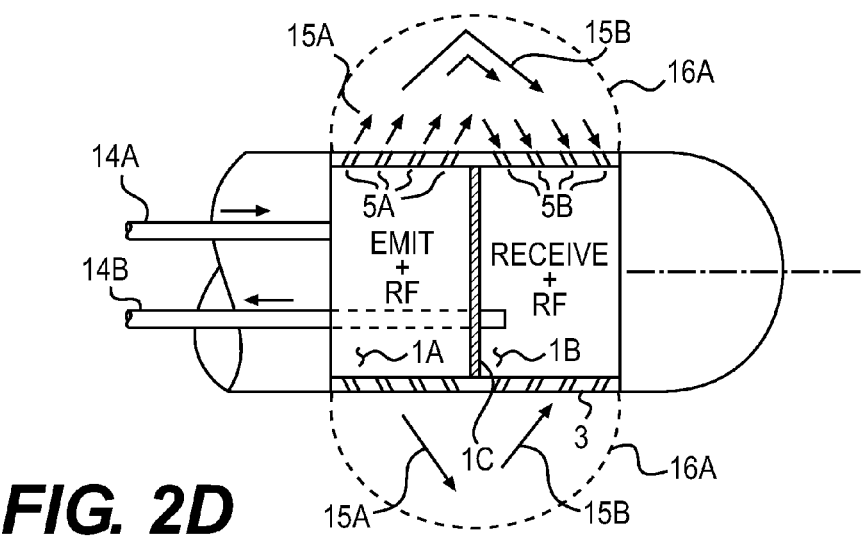
FIG. 2D illustrates lesion formation for an optical feedback RF ablator having a similar arrangement of optical and ablator elements as in FIG. 2B.
Figure 2E:
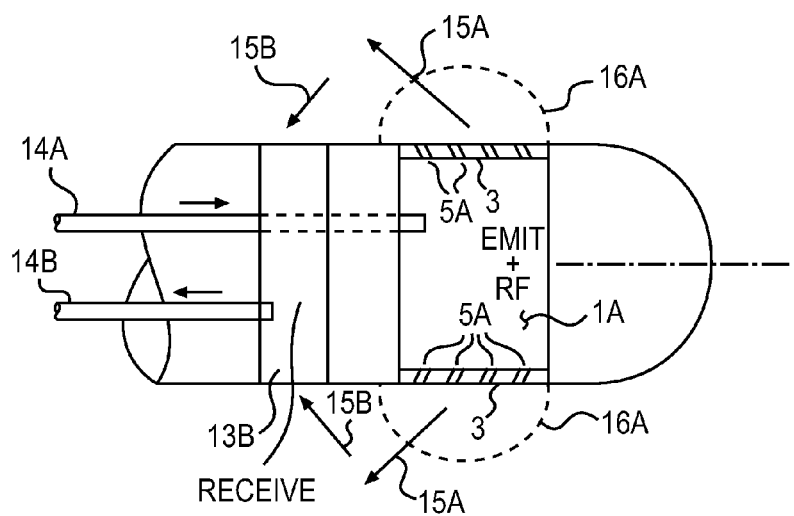
FIG. 2E illustrates lesion formation for an optical feedback RF ablator having an optical receiver separated from the ablation shell and serving only an optical receive function.
Figure 2F:
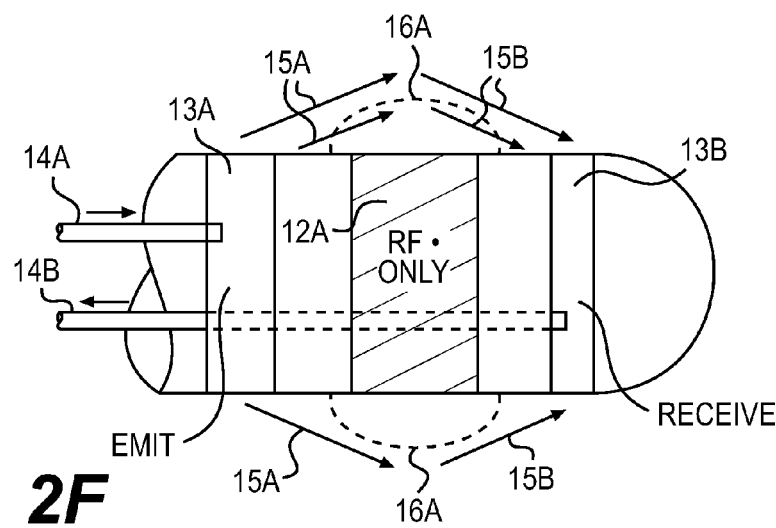
FIG. 2F illustrates lesion formation for an optical feedback RF ablator in which both optical transmitter and receiver are separated from the ablation shell as separate isolated transmitter and receiver.

There are three basic ways of lesion formation relative to the optical elements as illustrated in FIGS. 2D to 2F, although different variations and combinations are possible. FIG. 2D shows the same arrangement of the optical and ablator elements as FIG. 2B in which a lesion 16a forms both in front of the optical transmitter 1a and receiver 1b simply because both are also ablator portions due to their overlying RF shell or electrode material 3. In FIG. 2E, as opposed to FIG. 2D, the optical receiver 1b has been taken from under the RF ablation shell or electrode material 3 of FIG. 2D and situated separately as a receiver item 13b such that it now serves only an optical receive function. Thus it will be apparent in FIG. 2E that the lesion 16a will now form only in front of the combined optical emitter 1a and shell electrode 3 but not in front of the optical receiver 13b. If a larger lesion (than that depicted) is made, then eventually the lesion may also grow over the isolated receiver 13b as well. FIG. 2F shows that both the optical transmitter and receiver are no longer under the electrode shell 3 but are configured as separate isolated transmitter 13a and receiver 13b; neither 13a nor 13b serve an ablation function. Instead a bulk metal RF ablator 12a is disposed between the transmitter 13a and receiver 13b and spaced from them. It will be apparent that the lesion 16a of FIG. 2F will form as shown in front of the ablative portion 12a. Again, if the lesion gets much larger than that depicted, it may also eventually grow over one or both of the optical transmitter and receiver.

The light sources employable by the inventive devices may include, for example, continuously operated arc lamps, lasers or LEDs or, alternatively, pulsed arc lamps, lasers or LEDs. By "continuous" we mean for periods long compared to the summed optical travel time up and down the fiber and preferably measured in seconds or longer. The reader should recognize that that guarantees that there will be both rightwards and leftwards light occurring simultaneously. By "pulsed" we mean the light is "on" for a period shorter than the summed up/down propagation time mentioned above.

This guarantees some light is returning after the transmit light is stopped. The light source(s) of the inventive devices may be broadband (such as a halogen arc lamp) or narrowband (such as an LED or laser) or even narrowband and wavelength-scanning (such as by using a wavelength tunable laser). The returned light for both devices of FIGS. 2a and 2b could be detected in one or more manners such as by: (a) a wavelength scanning spectrometer, (b) a white light or monochromatic interferometer, (c) a light sensor such as a photodiode, CCD or CMOS chip. The ingoing light may be polarized or unpolarized. Polarized returning light will also show, upon lesioning, a polarization change or birefringence effect. Time domain reflectometry (TDR) may be useful for the sequential operation mode because one can discard or ignore the portion of the signal not coming from the tissue itself.

The reader will be aware of the use of bifurcated fibers wherein the two split legs of the bifurcated end are employed for transmit and receive respectively and the opposite single-end simultaneously (or sequentially) emits and collects light. Interferometry has the advantage of using optics to do time-gating (depth gating) faster than electronic circuits can do so. This is how OCT or optical coherence tomography works. TDR uses very fast electronics to detect and characterize fiber or light-path discontinuities (which would be the tissue portion of our optical path) but runs out of gas on short fiber lengths because of the very fast times. The present invention does not limit the methodology of how returned or received light is detected as there are several known methods to do so such as these; it only requires that at least some collected light is known to have backscattered from, reflected from or otherwise passed through tissue and can be optically modified by one or more optical interactions with the ablating or ablated tissue.

It is possible to employ a super fast picoseconds or femtoseconds laser in a pulse-echo mode to achieve the taught sequential approach, for example. However, long pulse or continuous optical sources are generally cheaper and more compact and provide better optical signal-to-noise performance because of the greater numbers of photons.

Note that for the dual cavity structure of FIG. 2B, the outgoing in-tissue light comes from chamber 1a and returning ingoing backscattered in-tissue light enters chamber 1b. Because these are physically separate, optically isolated, and laterally displaced chambers or optical elements, one can operate the emission light source continuously and have virtually zero unwanted tip-internal reflections which would degrade the S/N. This is a key aspect of the invention.

It will be obvious that any of the above embodiments can involve mathematically subtracting out and/or physically suppressing light which is internally reflected within the device. Further, before lesioning starts one can take a reference measurement of the intended target tissue and use that data as a baseline to compare to as lesioning causes returned light changes. Normalizing each lesion's data to its prelesion baseline is a nice way to exclude variations in light output or in tissue-coupling from lesion to lesion.

Before we proceed further it is important to discuss how the changing backscattering may be employed usefully. The term "returning light" is actually more globally correct than "backscattered" since it covers light which is (a) emitted and received from lesioned tissue (backscattered scheme) as well as the case wherein at-least one of the emission or reception optical elements is remote from the lesion and emits (or receives) light which travels both through lesioned tissue and surrounding or adjacent unlesioned tissue (the optical blocking scheme).

Increasing scattering also means decreasing penetration presuming one started with a relatively transmissive media or tissue as is typically the case for living human and animal cardiac tissue. If we arrange an optical emitter and an optical receiver to both be closely situated over a forming lesion in the backscattering scheme (e.g., using the device of FIG. 2b for example) we would expect the forming lesion in front of both emitter and receiver to backscatter more and more light back into the receiver as lesioning proceeds. This is indeed the actual case. However, if we provide a more distantly separated emitter and receiver (not depicted in figures) and we form the lesion only in front of one of them (the optical blocking scheme) we would expect that as lesioning proceeds we would see less and less received or returning light because in this arrangement the backscattering lesion is preventing light from passing through the lesion area due to its increasing local opacity and getting to the more distant receiver outside the lesion region which has not opacified or made opaque. This is also indeed the observed case. So one can see now that the up/down amplitude or intensity behavior of received or returned light depends on whether the lesion is formed in front of both, in front of just one, or in front of neither (lesion in between them) of the emitter or receiver. Note in the third approach one might even form the lesion between the emitter and receiver wherein one also sees a decrease in received light due to the opaque laterally blocking intervening lesion growing therebetween. Our invention only requires that any such change in received or returned light be monitored.

With further regard to the construction of the tip 3 in FIG. 2B, we note that the emitting optical vias 5a and receiving optical vias 5b are tilted toward each other (i.e., the two sets of vias 5a, 5b are not parallel with each other but the emitting vias 5a are tilted to direct light toward a tissue region and the receiving vias 5a are tilted to receive light from the same tissue region), thereby increasing the returned signal amplitude and concentrating signal coming from the lesioned region only. The optical vias are typically laser-drilled through the shell into the plug portions. It is again emphasized that an optical epoxy could be used to backfill such optical vias. The optical vias preferably act to direct outgoing and incoming light, such that each acts as a micro-miniature light pipe itself. With regard to the use of irrigation fluid such as water or saline, some or all of the vias may be filled out with flowed irrigation fluid rather than optical epoxy. To facilitate fluid flow through the vias, the plug may include fluid channels in the material or on its surface or the plug may be made of a material which is water-permeable. It is noted that for the device of FIG. 2B, there may be tens or even over a hundred such vias without substantially compromising the mechanical integrity of the shell/plug subassembly of the tip 3. This is because, unlike the mentioned prior art, our plug forms a mechanical foundation for the perforated shell everywhere. We note that the tip of FIG. 2A is depicted as having a forward facing optical via 5 (in addition to the side looking vias 5) and that although the tip of FIG. 2B does not depict forward looking optical vias, it could also employ them.

We again emphasize that it is preferable, but not absolutely required, that the tip employ saline irrigant for known and appreciated tip-cooling purposes. Such water or saline emission orifices may or may not simultaneously serve as optical vias or conduits in our devices. Our plug material might comprise a translucent or clear water-permeable material (bulk permeable) such that irrigant water can flow through it and out irrigant-only or irrigant/optical orifices. A practical advantage of a water permeable plug is that water inflow into irrigant orifices comes from all directions and such flows are unlikely to be all interrupted by particulates, thrombus or clot.

Also note that a water permeable plug material may be substantially more light-transmissive after it is bulk-permeated.

It appears that the use of a full emitted broadband optical spectrum may not be required for lesion feedback and that the use of only one or a few specific wavelengths may be sufficient presuming these wavelengths are ones known to be sensitive to lesioning. In this manner, lesion feedback may employ one or more monochromatic sources or even one or more wavelength-tunable sources. In that case, photo-detectors or CCDs sensitive to the wavelength(s) involved may be used as light analyzers instead of a spectrometer which is required to scan many wavelengths such as for looking at a broadband spectrum which has been backscattered. The received spectrum has amplitude versus wavelength behavior which is a result of both increasing backscatter with lesioning and known optical absorption lines related to in-tissue species such as hemoglobin and water.

The catheter tip according to embodiments of the present invention differs from prior catheter tips that utilize a hollow cavity as the interior emission chamber. The present tip has a glass, polymer, or epoxy plug body through which light can pass through at least one of the plug material itself, through drilled or formed optical vias or conduits in the plug material, or through formed optical vias or conduits which are then backfilled with saline or optical epoxy. The tip has a plurality of optical emanation and reception holes and all of these holes do not need to be fluid emanation holes. For example an optical via or conduit may be filled with or occupied by moving or nonmoving saline or nonflowing or solidified optical epoxy or plug bulk material. The via-overlying thin portion of metallic shell material would be removed to allow light to pass. This preserves the mechanical integrity of the overall tip yet allows a considerable number of holes to achieve a screen-like electrode with a significant area-percentage of optical vias having a large total collection area. Such a screen-like electrode/plug can be easily electroformed, laser drilled, and cast full of optical epoxy which also fills out the shell vias to the surface. We include in our inventive scope the use of an orifice-containing metallic shell as a mask for etching or laser drilling optical vias into underlying plug materials. Alternatively a laser can drill through both a shell and then through plug material to form such optical vias and/or irrigant vias through and into both.

According to a specific embodiment based on the features described above, an RF ablation catheter has a tip which both thermally ablates and performs as an optical sensor for the ablation process involving the use of an RF power source and associated power control circuit(s) or logic. The ablation catheter includes a proximal control handle; a catheter lumen and body connecting the proximal handle to a distal tip; and a distal ablation tip. The ablation tip construction includes a glass or polymeric thermoformed, machined, molded or cast plug, a metallic shell enwrapping the plug, the shell being electroformed, plated or mechanically formed; at least one optical via passing through the shell into (or to) the plug, at least one optical fiber or conduit passing through the lumen or catheter body to the tip plug and optically coupled to the plug which plug is in turn coupled to target tissues by the tip optical vias; preferably flowed irrigant preferably passing through the catheter body or lumen into and out of the tip, the irrigant at least cooling the tip during or after RF ablation; a light source coupled to a proximal fiber to deliver light at at least one wavelength to the tip or a light source mounted in any portion of the catheter and capable of delivering such light for emission from the tip; and a light analyzer or spectrometer coupled to a proximal fiber in order to detect changes in at least one wavelength of returned light as lesioning proceeds, the changes in reflected, attenuated or backscattered light caused by the lesioning, the tissue scattered light received by the analyzer from the tip through the one or more optical fiber(s) or conduit(s). Any irrigant orifices may or may not double as optical vias.

According to another specific embodiment based on the features described above, a thermal ablation catheter for ablating tissue has a tip which both ablates and performs as an optical monitoring or control sensor for the ablation process involving the use of a thermal ablation power source and associated power control circuitry or logic. The catheter includes a proximal control handle; a catheter lumen and body connecting the proximal handle to a distal ablation tip and containing at least one optical conduit or fiber; a distal thermal ablation tip comprising a metallic or metal-containing shell and an interior plug material; at least one source of illumination whose light can be emanated from the tip into tissue adjacent the tip through one or more tip optical vias. The tip is also capable of inwardly receiving tissue-backscattered or reflected emanated light through one or more tip optical vias. The received backscattered light is returned to the handle region or external the patient using at least one optical fiber or conduit in the catheter lumen or body. The returned light is analyzed by one or more instruments for changes to one or more spectral parameters caused by the lesioning process. Again, depending on fiber arrangments discussed above, the inherent increasing backscattering with lesioning either causes an increase in backscattered light when both emitter and receiver optical vias both sit on the lesion—or cause a blocking reduction or attenuation in light received by a receiver from a more distant emitter wherein only one of those sits on the lesion. Both emitter and receiver may be off-lesion in which case the growing more-opaque in-between (or even adjacent) lesion also acts as a blocker or as a reflector.

Figure 3:
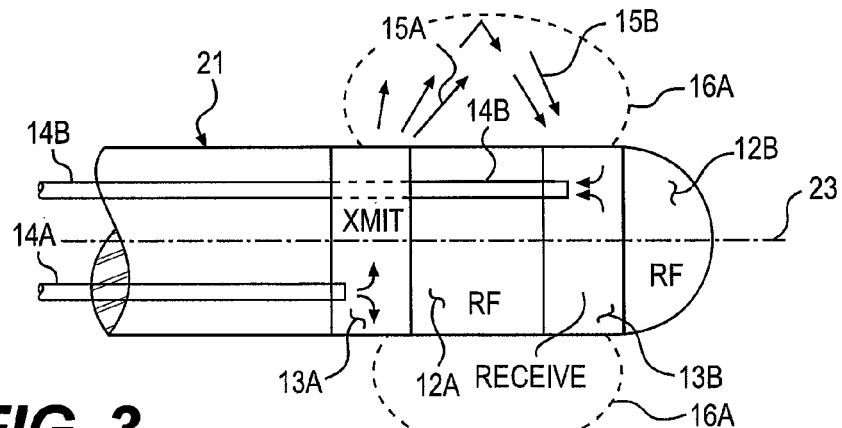
FIG. 3 schematically illustrates an optical feedback RF ablator with side-looking optical feedback.

FIG. 3 schematically illustrates an optical feedback RF ablator with only side-looking optical feedback. The side-looking optical feedback preferably spans 360 degree around the longitudinal axis 23 of the catheter 21. In FIG. 3, an RF ablation catheter 21 includes a catheter tip which has two RF ablating portions 12a and 12b and two optical element portions 13a and 13b. The RF cylindrical portion 12a forms sideways lesions whereas the RF tip portion 12b forms tip-forward lesions. The RF ablating portions 12a and 12b may be constructed as metallic shells around glass or plastic plugs similar to those shown in FIGS. 1 and 2. Alternatively, the RF ablating portions 12a and 12b are solid metallic portions having channels and/or cavities to accommodate wires, irrigation fluid flow, and the like. The solid metallic portions 12a, 12b are bonded or otherwise attached to the optical element portions 13a, 13b that are made of glass, polymer, or the like (e.g., by molding the optical element portions onto the solid metallic portions).

The optical element portion 13a is the light emitter or transmitter. The optical element portion 13b is the scattered light receiver. The optical emitter 13a (illumination optical element) is fed light via an emission optical fiber or conduit 14a. The optical receiver 13b (collection optical element) returns scattered light via an optical reception fiber or conduit 14b. Note that some amount of light leaves emitter 13a as light 15a and scatters from tissue to return as light 15b to the optical receiver 13b. This first example device only provides side-looking optical feedback and not forward-looking optical feedback. Ablation lesions from which optical feedback can be obtained are depicted as side regions 16a. The emittable light arriving via the emission fiber 14a will be broadband white light (e.g., from an arc or halogen lamp) or will be one or more selected wavelengths (or wavelength windows) of light such as provided by wavelength-specific LEDs, fixed wavelength lasers or tunable lasers. The returned scattered light 15*b* will be spectroscopically analyzed (if it is broadband white light) such as by using an Ocean Optics 2000+ USB spectrometer connected to the reception fiber 14*b*. Changes in the amplitudes of particular wavelengths and of whole portions of the returned scattered spectrum are known to occur when tissue is thermally ablated and ultimately necrosed. In specific embodiments, the emitted light may include any one or more of broadband light, broadband white light, light of a particular wavelength, light of two or more particular wavelengths, light of a wavelength that can be tuned, CW (continuous wave) or pulsed light, and incoherent, coherent, or polarization-controlled light.

Before proceeding further it will be useful to mention what physical mechanisms we have discovered which can cause backscattering (and associated transmissive attenuation). When heating tissue above body temperature by any means (RF, laser, microwave, HIFU, etc.) one causes microbubble evolution because bodily gases such as oxygen, nitrogen and $CO_2$ are less soluble in warmer liquids. Such evolved bubbles are optically highly backscattering and transmissively blocking. A completely different mechanism is steam bubbles wherein the temperature is much higher and in the vicinity of 100 deg C. (at least in the bubbles). Even blood with no gas dissolved in it could form steam bubbles if it approaches 100 Deg C. These steam bubbles may grow from the water turning to steam in the blood but may originally nucleate on the prior above precipitating solute micro bubbles for example. In general steam bubbles are larger and get larger much faster and forcibly than the prior gas-solute reduction microbubbles. It is steam bubbles which create audible pops and even explosive tissue cratering in the worst cases. We have observed in our optical feedback (wherein both emitter and receiver sit on the lesion) data that a steam pop involves first a rise in backscatter and then a precipitous plunge in backscatter upon popping as a tissue flap is created. Further we have observed that even before an actual audible pop there exist inaudible prepops which also involve rises and falls in backscatter. However the audible pop actually appears to substantially vent itself and occurs at a point of maximal backscatter and shows a huge drop in backscatter upon popping. The audible pop frequently occurs after a string of 2-5 lesser inaudible (pre)pops each of which jacks up the net backscatter level more and more in a staircase fashion. Thus the point here is that the preceding nonventing inaudible pops can be optically seen to warn of an impending venting (audible) pop such that the power can be turned down to avoid said audible venting pop.

Optical backscattering is also seen returning from the structure of the tissue itself as it whitens and browns during lesioning. Essentially the denatured protein-crosslinked tissues are increasingly opaque particularly in the visual wavelengths as can be also seen with the naked eye. Thus the optical technique sees BOTH microbubbling phenomenon and structural scattering phenomenon both of which act to increase backscatter and block transmitted light.

Figure 4:
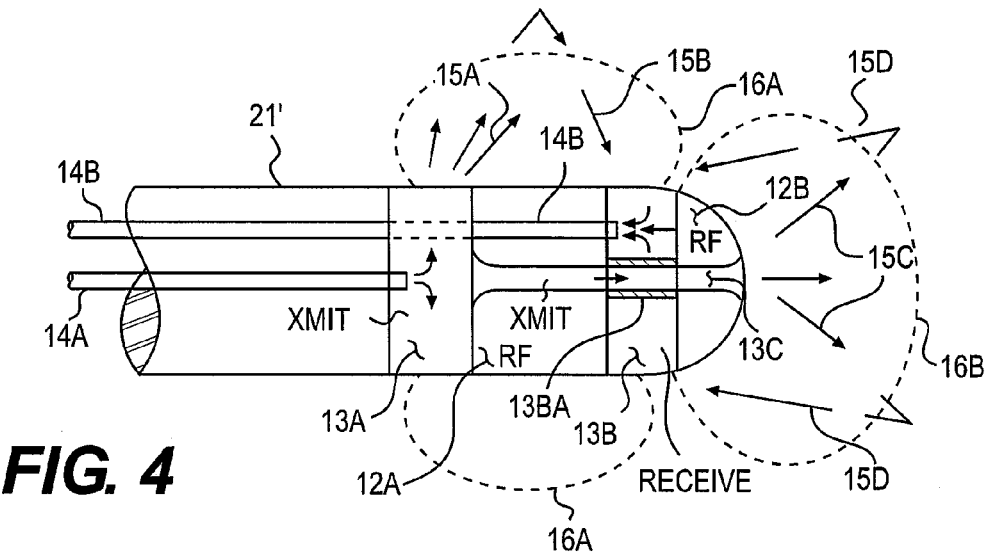
FIG. 4 schematically illustrates an optical feedback RF ablator with side-looking and forward-looking optical feedback.

FIG. 4 schematically illustrates an optical feedback RF ablator with both side-looking and forward-looking optical feedback. The side-looking optical feedback preferably spans 360 degree. The RF ablation catheter 21' is similar to the catheter 21 of FIG. 3, but with additional features to provide forward-looking optical feedback. The transmit or emitting optical component 13*a* now also has an extension 13*c* extending forward to the outer tip end-face of the RF tip portion 12*b*. In this manner, the transmit component 13*a*/13*c* provides emitted light generally sideways as light 15*a* and generally forward as light 15*c*. The device of FIG. 4 retains the single optical receive element 13*b* which is now shared between side returning light and forward returning light. Therefore, both the sideways returning scattered light 15*b* and the forward returning scattered light 15*d* will be received by the receiving optical element 13*b*. Ablation lesions from which optical feedback can be obtained are within the side lesioned region 16*a* and the forward lesioned region 16*b*. Note that where the transmit optical element portion 13*c* passes through the receiving optical element 13*b*, the device optically masks the two light paths from each other utilizing an opaque material or film 13*ba*. In specific embodiments, the illumination optical element 13*a* and/or collection optical elements 13*b* each comprise a substantially annular optical element that optically emits or collects light throughout most or all of 360 degrees around the longitudinal axis (preferably at least about 90%, more preferably at least about 99%, and most preferably about 100% of 360 degrees of light emission or collection.

The illumination or emission optical element and the collection or reception optical element can be made of one or more of the following: a cast polymer or epoxy having optical conductance or transmissivity, an injection molded polymer having optical conductance or transmissivity, a refractive index controlled polymer having optical conductance or transmissivity, and a molded, machined, or ground glass material having optical conductance or transmissivity. The optical fibers can be optically coupled with these optical elements by molding or casting the optical element around the optical fiber or inserting the optical fiber into the optical element using an optical coupling material such as an optical epoxy or optical gel having a refractive index which maximizes transmission through the interfaces involved in the well known manner. We remind the reader that the plug material might be water permeable and if so it might achieve increased optical translucency or transparency upon said permeation. The plug material could also be permeable and opaque (or nonpermeable and opaque) requiring all optical vias to be drilled all the way to their respective fiber(s). This is workable but less preferred. Again we include the case wherein some or all of the optical vias are provided by saline or water paths.

Figure 5:
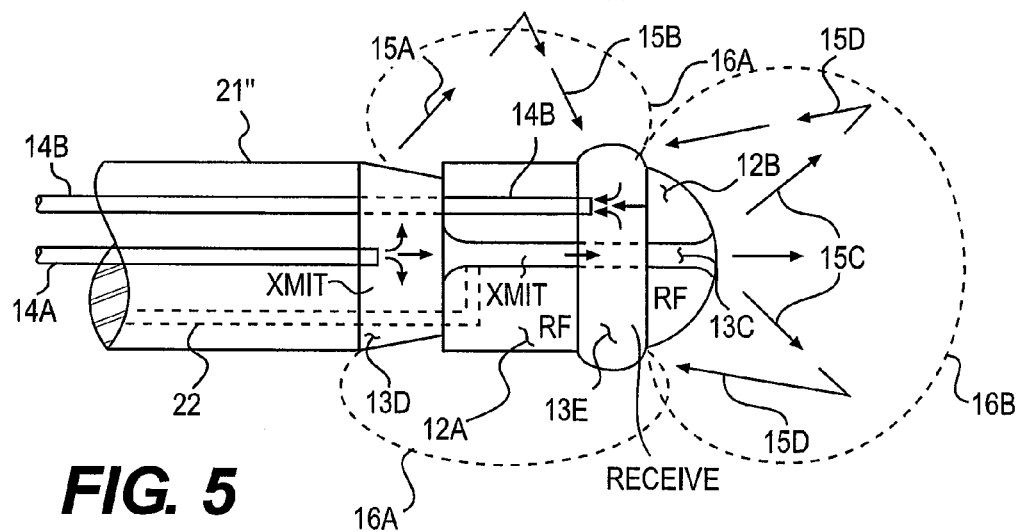
FIG. 5 schematically illustrates an optical feedback RF ablator with side-looking and forward-looking optical feedback and enhanced optics.

FIG. 5 schematically illustrates an optical feedback RF ablator 21" with side-looking and forward-looking optical feedback and enhanced optics. As compared to FIG. 4, the emitting optical element 13*a*/13*c* is replaced by 13*d*/13*c*, and the receiving optical element 13*b* is replaced by 13*e*. The optical transmit or emission element portion 13*d* is angled such that its outer surface casts emitted light at an angle more tip-forward toward the RF tip portion 12*b*. The optical receive element 13*e* is shaped in a convex manner on the outer surface such that it can collect more scattered light 15*b* and 15*d* from the side region and the tip region, respectively. The optical emission element portion and optical receive element portion are shaped (or unshaped or less shaped and index-graded such as for a GRIN lens) such that light emission and light reception take a substantially angled departure from the normal or perpendicular direction with respect to the longitudinal axis of the catheter body. This feature of shaped optical elements such as annular lenses is somewhat similar in effect to the tilting of optical vias employed in the structure of FIG. 2B. These optical element shape modifications of FIG. 5 (relative to FIG. 4) can improve the signal-to-noise or S/N ratio of the device significantly. FIG. 5 further shows an irrigation fluid channel 22 coupled with the emitting optical element 13*c* which may be hollow (liquid filled) or liquid-permeable. That is, the emitting element conduit 13*c* is at least partly a saline or water filled optical lumen. Of course, the ablation tip may include multiple irrigation fluid channels having different configurations. Again receiving element 13e is preferably shared between sideways and tip-end returning light.

At this point it is useful to mention that with an inventive catheter one would likely make either a sideways lesion or a substantially forward lesion, but not both simultaneously as is the case today without any such optical feedback. It is known that any lesioned tissue is much more reflective and backscattering than nonlesioned tissue for the microbubbling and tissue-structural scattering reasons described above. Therefore, it follows that even for a shaped lens structure such as that of FIG. 4 or FIG. 5 even if only one lesion type (side or tip lesion) is being formed at a given time that one will still see an appreciable increase in scattering despite the fact that the other potential lesion area seen by the receive lens is not being lesioned also. Again, a baseline reading taken before forming the side lesion would provide a zero reference.

Figure 6A:
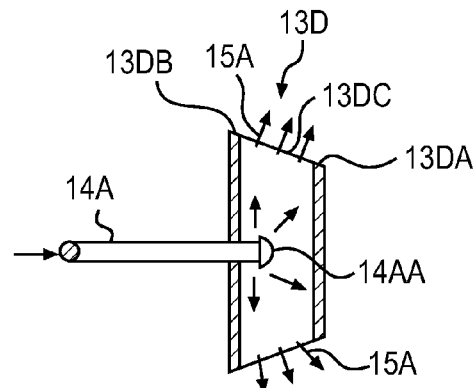
FIGS. 6A and 6B illustrate the optical transmit or emission element portion of FIG. 5.
Figure 6B:
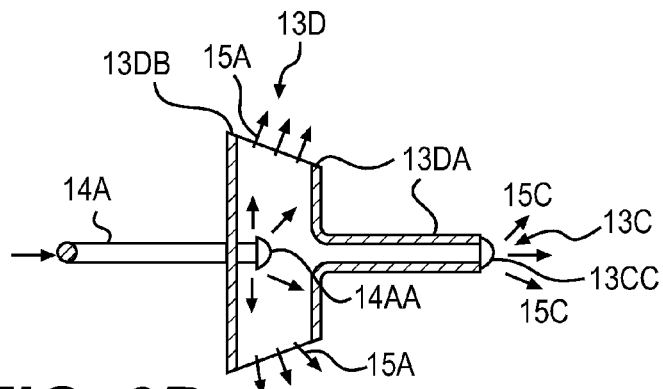

FIGS. 6A and 6B illustrate the optical transmit or emission element portion of FIG. 5. FIG. 6A shows in more detail the angled transmit or emission optical element 13d. Of particular interest is the two-part emitter element 13d/13c in FIG. 6B which is the dual emitter component seen in FIG. 5. The dual (sideways and forward) emitter of FIG. 6B preferably is injection molded from an optical grade polymer or is cast from an optical grade epoxy. FIGS. 6A and 6B depict opaque light-blocking layers 13db and 13da which are preferably highly reflective on the emitter element interior side. These assure that emission light in emitter element 13d/13c ultimately makes it out of the element as emitted light 15a even if that requires more than one light bounce or reflection event. FIG. 6A shows an inclined surface 13dc for emitting light. FIG. 6B shows a diffusing or beam-spreading lens or numerical aperture 13cc on the tip of the optical element 13c for emitting light. Note that in FIG. 6B, the input optical fiber 14a delivering light to be emitted is approximately centered on the optical element 13d/13c such that roughly half the light is emitted by the emission optical element portion 13d as light 15a and half by the optical element 13c as light 15c. The transmit optical elements of FIGS. 6A and 6B include the emission fiber 14a, which is depicted as having a lens 14aa on its tip inside the emission optical element portion 13d. The lens 14aa may be a GRIN lens or ball lens or may be simply be a beamspreading or diffusing numerical aperture of the fiber tip itself. This might be used, for example, to enhance radial light emission or to controllably split the radial and forward emission activity. Such a tip lens could comprise a standalone manufactured lens, a modified fiber tip, or even a cast-in place polymeric entity. In specific embodiments, an additional optical component such as a mirror, prism, or lens such as a GRIN lens can be employed to more favorably couple an optical fiber to an emitter optical element or a receiver optical element or to more favorably distribute light to or from an emitter optical element or a receiver optical element.

FIGS. 6a and 6b depict the emitting lens structure as being a standalone component. We emphasize that one or both of the emitting and collecting lenses may be molded directly to the metallic RF tip portions in a mold instead. In that case the opaque reflective layers 13db/13da of FIG. 6b may be replaced by the inherent opacity and reflectivity of the adjacent RF metallic tip components. Such direct molding processes assure that the reflectivity of such bonded interfaces can be predicted and relied upon to be stable.

Figure 7:
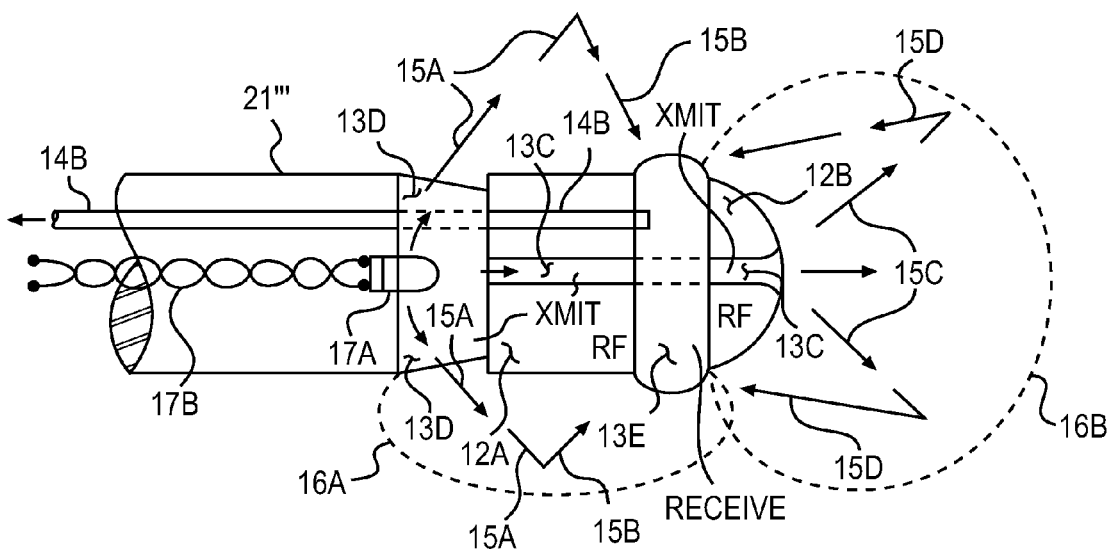
FIG. 7 schematically illustrates an optical feedback RF ablator with side-looking and forward-looking optical feedback utilizing tip-mounted light source(s).

FIG. 7 schematically illustrates an optical feedback RF ablator with side-looking and forward-looking optical feedback utilizing tip-mounted light source(s) 17a. The optical-feedback RF ablation catheter 21''' is similar to that of FIG. 5, but utilizes an in-tip or in-catheter light source 17a instead of an emitting delivery fiber 14a. The light source 17a would likely have electrical leads 17b routed down the catheter lumen leftwards (toward the proximal end of the catheter). We note that the light source might be a laser, a VSCEL laser, an LED, a bulb, a halogen lamp, or an arc lamp, for example. The light source 17a may be white (broadband) or may be of a specific wavelength or wavelength range or might even be electrically wavelength-tunable. It may comprise a wavelength tunable source or a group of sources each having a different wavelength and grouped to deliver one or more of their outputs individually or simultaneously to a common output path. An advantage of the on-board light source, particularly if fixed wavelength(s) are to be emitted, is that the catheter lumen can then contain a bigger diameter reception fiber 14b for better sensitivity and S/N ratio.

As with irrigated catheters, the present design will preferably route outflowing (or less preferably recirculated) irrigation fluid such as saline through, near or past the metal shell portions of the RF tip to cool it and its contents which include the optical emitter and receiver. The near tissue-field and tip cooling which results will also thermally protect the optical elements, both by flowing irrigation fluid past their faces and by the adjacent metallic RF parts being cooled directly and being excellent heat sinks for the lenses. One may also choose to route the irrigation fluid through the optical elements themselves as for our aforementioned water-filled, water-containing or water-comprising optical vias. For instance, the optical elements may be permeable to the irrigation fluid such as water, saline, or the like as described above, or may be composed entirely of saline or water irrigant. Lenses might also include water lumens which simply allow water passage through or along the lens to another location.

As discussed above, some embodiments may use saline flow paths as liquid optical "fibers" or conduits wherein the fiber or conduit is, for example, a) a water filled otherwise empty path, or b) a water saturated or permeated path through a bulk permeable material which is opaque or translucent when saturated. This approach can even extend to making the optical elements (emitter and receiver) comprise water containers or defined volumes with clear walls or even with no walls on the outside tissue-facing surfaces. In addition, the present design may save packing space in the catheter lumen by coating/wrapping optical fibers with metal/braid and thereby also using them as electrical power/signal/data lines.

Figure 8:
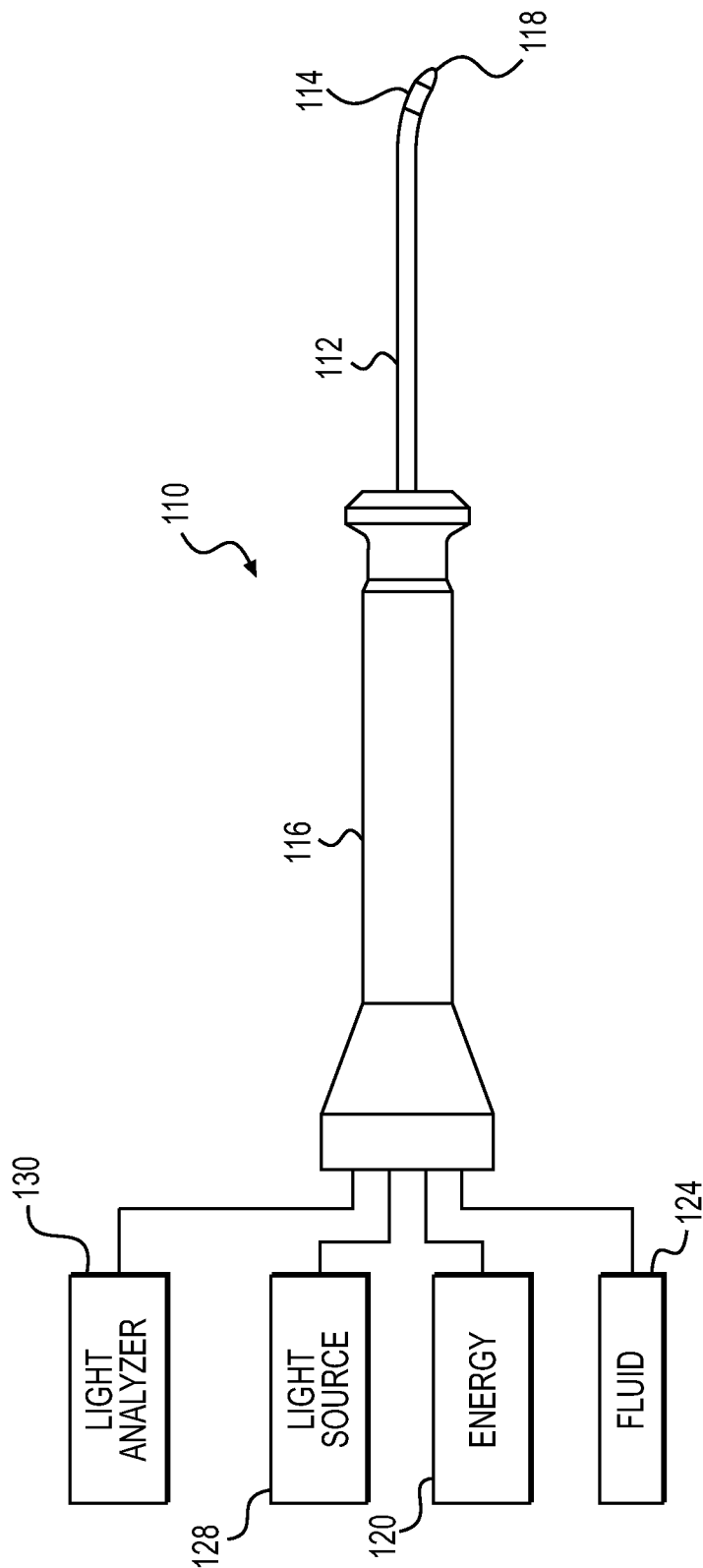
FIG. 8 is a schematic diagram of an apparatus for RF ablation with optical feedback.

FIG. 8 is a schematic diagram of an apparatus for RF ablation with optical feedback. An ablation catheter 110 includes a control handle 116, and an elongated catheter body 112 having a distal region 114 adjacent a distal end 118. The distal region 114 includes any of the ablation/feedback tips shown and described above. The catheter 110 is connected with an energy source 120 such as an RF generator for ablation, and preferably with an irrigation fluid source 124 to provide irrigation fluid. A light source 128 supplies light to the distal region 118 of the catheter 110, which may be any of broadband (white, multiple wavelengths) light, laser light (single wavelength), and the like. The external light source 128 is not needed if an internal light source is instead provided within the catheter tip or handle. A light analyzer 130 such as a spectrometer, interferometer, or one or more photodetectors of CCDs is provided for analyzing the light collected to evaluate the tissue lesioning during ablation. The light analyzer(s) 130 may include a quantification component that translates one or more measured light parameters such as intensities or diffraction patterns into electrical signals that can be processed with a computer and displayed graphically to an operator of the catheter 110. In this way, information regarding parameters of the tissue lesioning is provided to the operator and/or to the ablation system itself to provide real time assessment of the ablation and the possibility of user responsive control or automatic system control.

We have shown in the above figures the light analyzer(s) being external to the catheter device and handle as in FIG. 8. As for the emitter light-in-tip device of FIG. 7 we also include in our scope the option of having a light analyzer in the catheter tip or handle. This is particularly realistic in the case of the light analyzer being photodetector or CCD based as photodetectors and CCDs can be small and inexpensive.

According to a specific embodiment as described above, a thermal tissue-ablation catheter has a distal ablating tip, an intermediate extended lumen or catheter body, a proximal control handle, a source of ablation power coupled into the distal tip, and an optical lesioning-feedback subsystem. The catheter includes at least one substantially annular optical emitter element fed by an optical energy delivery fiber or source, the emitter emitting light into tissue for scattering therein or there from; and at least one substantially annular optical receiver element receiving at least some of the scattered light and feeding a returned scattered-light reception fiber or detector. The at least one emitter and at least one receiver are spaced apart such as by an ablating tip portion or can even be adjacent one another and juxtaposed on both outer sides by, for example, RF ablation tip portions. Emitted light will interact with a forming lesion depending on ablator/emitter/receiver relative positions such that it affects received light as by aforementioned increased backscattering or decreased signal due to blocking lesion opacity. The received scattered light is affected with respect to an optical parameter by the lesioning action or state of lesioning in the tissue. Such a parameter could include net increases seen in reflective or backscattered amplitude at one or more wavelengths as lesioning progresses in front of an emitter/receiver pair and/or the resulting changing slopes of the spectrum in various wavelength ranges. The received light thereby undergoes changes which correlate with or can be used to qualitatively or quantitatively estimate, measure, monitor or track lesioning progress (i.e., increased scattering and opacity). As used herein, "substantially annular" means that the outgoing or incoming light leaves or enters one or more of the optical elements wherein the at least one optical element comprises two or more separate sub-elements distributed around the circumference or around the 360 degree range, the optical element thereby comprising multiple sub-elements distributed around the 360 degree circumference. In one scenario wherein emitter and receiver both face the growing lesion one correlates, during product design and development, the received light spectrums versus increasing lesion-depth (and therefore versus lesion volume), bigger and deeper lesions having progressively higher amplitude spectrums with changed slopes up to a saturation lesion depth. Normalization of each spectrum to its pre-lesion spectrum may also be employed. Knowing this correlation and recording that correlation in the form of a lookup table or mathematical relationship, one can have the system report estimated lesion depth (and lesion volume if desired) based on the spectrum observed.

In a second scenario the lesion is formed in front of only one of the emitter or receiver and this means that light received by the receiver will decrease as lesioning progresses because the growing lesion is blocking the lights passage between emitter and receiver.

It will be apparent that one could make a design wherein a smaller growing lesion first decreases light and then when it is big enough to cover both emitter and receiver it increases light after that. Note that in this approach the emitter/receiver spacing specifically indicates when the lesion size equals the spacing as evidenced by said change in optical amplitude direction.

In a preferred embodiment the returned scattered light is directed to a wavelength scanning spectrometer or to a specific wavelength-sensitive photodiode. Both can sense the backscattered intensity amplitude at given wavelengths. The optical spectrometer analyzes returned scattered light in order to monitor or track one or more of: lesion progress, lesion volume, lesion depth, steam-pop potential or occurrence, presence of char, presence of clotted blood or thrombosis, tissue proximity, angle to tissue, tissue force. Each of these phenomena causes discernable unique backscattered spectrum changes versus time and power.

Observed backscattering or opacification changes of the lesioning tissue are due to the increased concentration of the burned constituents of the tissue (e.g., denatured proteins), the loss of water content, the oxidation/burning of blood constituents such as hemoglobin, the formation of char, and micro bubbles which evolve or form due to tissue heating as by one or both of dissolved gas-dissolution and steam generation. We again stress that steam related bubbles can grow very large (millimeters) and can cause audible pops and the raising of thin tissue-flaps if not outright cratering. We have seen again that the evolution of pop-related flaps filled with gas or liquid for at least a short period result in a precipitous drop (after an extended rise) in backscattered light. In all of the embodiments discussed so far the returned backscattered light is at least some of the light which was emitted into the tissue. Also included in our inventive scope is the additional (or alternative) observation of optical fluorescence excited in prelesioned and lesioned tissues by our emission light and even observation of radiated infrared wavelengths which constitute IR thermography. Pulsed IR fluorescence is a rapidly growing field and may be practiced with or without fluorescent dyes introduced into the target tissues.

In the fluorescent excitation mode, the transmitted light excites different newly created (excited) returning light. That is, the originally transmitted returned (backscattered) light, if any, is not what is measured. What is measured is newly excited light that is characteristic of the fluorescence of certain cell types (e.g., nerve cells, specific cells associated with arrhythmia, dead cells such as ablated cells), or cell or blood constituents or that is characteristic of a fluorescent dye administered to the patient which preferentially distributes itself at similar targets of interest. Note that the transmitted excitation light is wavelength-chosen to excite the specific (typically different) wavelength fluorescence in the known manner of fluorescence microbiological imaging. Typically for fluorescence imaging a short-pulse laser is employed for illumination (e.g., femtoseconds, picoseconds, microseconds range) as this will excite the fluorescence but be short enough not to "wash it out" by over saturation or "bleaching." Note that this illumination is very different than long CW illumination for our above backscattering lesion feedback—and that the returned light is new light of a likely different wavelength and a likely much lower intensity. The different wavelength makes detection easy since it cannot be confused with the transmitted excitation light. Since for fluorescence the light source is typically pulsed, the same fiber can be used to both transmit the fluorescence excitation pulse(s) and (subsequently) receive the excited responsive fluorescence pulse. There is a biophysical delay in the returning fluorescence pulse and that returned pulse usually is relatively long and exponentially decaying. Alternatively one could fluorescence-mode transmit and receive on separate fibers. Reduction in such fluorescence behavior coming from disappearing nonlesioned tissue or an increase in fluorescent behavior associated with increased amounts of damaged tissues accumulating such a dye could, for example, be employed to track lesion progress.

The present construction has several significant advantages over prior designs. Such advantages include:

a) Avoidance of optical vias which need to be optically isolated along their via lengths, which are difficult to manufacture and prevent optical leakage between so many tiny transmit and receive paths;

b) Tilted or shape-directed or GRIN-based optical orifices or vias to increase the amount of emitted/returned signal in particular tissue target regions such as those next to RF metallic tip portions;

c) Options for solid-like tip having very good structural integrity;

d) Option for use of permeable plug material, whether itself translucent or opaque, allowing for flow through plugs and therefore cooled plugs/metallic shell despite the fact that the plug material may not be an excellent thermal conductor e) Use of microinjection polymeric molding for lenses, resulting in low cost and high precision;

f) Use of molded lenses which are molded or cast directly to the metallic RF parts;

g) Axial separation of transmit and receive elements, thereby minimizing returned light which hasn't scattered from tissue and avoiding the need to optically isolate large number of transmit (or receive) optical vias from immediately surrounding receive (or transmit) optical chambers;

h) Annular lenses allowing for large optical apertures without compromising structural integrity of the tip;

i) Use of electroforming technology-particularly where a polymeric or glass plug serves as the mandrel, or where the electroformed shell serves as a polymeric casting vessel;

j) Lenses which act both sideways and forwardly (parts reduction);

k) Ability to make the device with only two lenses (parts reduction);

l) Spaced lens/RF/lens sequences along axis of tip;

m) Continuous or pulsed modes operation;

n) Option to place one or more of light sources or reception detectors in handle or in tip, particularly for tiny LEDS/lasers and tiny photodetectors;

o) Use of flowed liquid filled optical orifices which can flush away surface bubbles, thrombus and clot; and p) Use of either or both of emitter/receiver/ablator element relative positioning which causes backscattering light increases, transmitted light decreases or both in sequence as the lesion grows laterally or depthwise.

Finally the inventors have also noted that the optical feedback can vary as a function of tip application force and particularly how enwrapped, buried or embedded the tip becomes in the tissue upon increasing force as more of the optical element circumference is in intimate tissue contact. We specifically claim the use of such force-dependent optical behavior both as a means to estimate force for its own sake (such as to avoid dangerous tissue puncture or to assure a minimal desired load) and to account for or compensate for any variation in optical output simply because the force affects said output. Also included in the scope is the provision of an independent tip force sensor to provide this force information, the force sensor possibly being optical in nature and possibly sharing one or more optical components with the lesion feedback optical elements/fibers and supporting hardware/software.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. An ablation catheter comprising:
    an elongated catheter body extending longitudinally between a proximal end and a distal end along a longitudinal axis; and
    at least one ablation element carried by the elongated catheter body to ablate a targeted tissue region outside the catheter body;
    an illumination or excitation optical element disposed adjacent the at least one ablation element, the illumination optical element being light-transmissive to emit light from the illumination optical element to the targeted tissue region;
    a collection optical element disposed adjacent the at least one ablation element, the collection optical element being light-transmissive to collect one or more of returned, backscattered or newly excited light from the targeted tissue region in response to the light emitted from the illumination or excitation optical element to the targeted tissue region; and
    a barrier disposed between the illumination or excitation optical element and the collection optical element to substantially prevent light from traveling between the illumination optical element and the collection optical element along a path within the catheter body,
    wherein the illumination or excitation optical element and the collection optical element are axially spaced from one another and axially optically isolated from one another by the barrier.

2. The ablation catheter of claim 1, wherein the barrier comprises an opaque member.

3. The ablation catheter of claim 1,
    wherein one or more of the illumination optical element or collection optical element each comprise an annular optical element.

4. The ablation catheter of claim 1,
    wherein the at least one ablation element comprises a metallic shell which at least partially covers the illumination optical element and the collection optical element; and
    wherein the metallic shell includes a plurality of first openings through which to emit light from the illumination optical element to the targeted tissue region and a plurality of second openings through which to collect, by the collection optical element, light from the targeted tissue region in response to the light emitted from the illumination optical element to the targeted tissue region.

5. The ablation catheter of claim 1,
wherein the illumination optical element has one or more interior surfaces covered by opaque light-blocking layers; and
wherein the collection optical element has one or more interior surfaces covered by opaque light-blocking layers.

6. The ablation catheter of claim 1,
wherein at least one of the illumination optical elements emits light or the collection elements receives light, along at least one path, oriented at an angle of between about 90 degrees and zero degrees relative to the longitudinal axis.

7. The ablation catheter of claim 6,
wherein the illumination optical element includes a plurality of illumination optical vias oriented at an angle relative to the longitudinal axis but having a directional component along the longitudinal axis toward the collection optical element; and
wherein the collection optical element includes a plurality of collection optical vias oriented at an angle relative to the longitudinal axis but having a directional component along the longitudinal axis toward the illumination optical element.

8. The ablation catheter of claim 7,
wherein at least one of the illumination or collection optical vias comprises a light conduit for light to travel through, the light conduit including, at least in part, a material selected from the group consisting of liquid, polymer, glass, transparent material, and translucent material.

9. The ablation catheter of claim 6,
wherein the illumination optical element includes an illumination annular lens to direct light at an angle relative to the longitudinal axis but having a directional component along the longitudinal axis toward the collection optical element; and
wherein the collection optical element includes a collection annular lens to receive light at an angle relative to the longitudinal axis but having a directional component along the longitudinal axis toward the illumination optical element.

10. The ablation catheter of claim 1,
wherein the at least one ablation element includes a side-ablating element disposed between the illumination optical element and the collection optical element.

11. The ablation catheter of claim 1,
wherein the at least one ablation element comprises a first ablation element which is axially situated at an axial distance equal to or greater than zero from the illumination optical element and an axial distance equal to or greater than zero from the collection optical element.

12. The ablation catheter of claim 1,
wherein an ablation element includes a metal-containing, electrically conductive electrode material.

13. The ablation catheter of claim 1,
wherein the at least one ablation element includes a forward ablation element disposed at the distal end and adjacent the collection optical element.

14. The ablation catheter of claim 13,
wherein the forward ablation element comprises a metal-containing solid member having a rounded atraumatic shape.

15. The ablation catheter of claim 13, further comprising:
a light conduit running axially inside the distal portion, the light conduit for at least one of delivering emitted light to the illumination optical element or receiving returned light from the collection optical element.

16. The ablation catheter of claim 1, further comprising:
a first optical fiber in communication with the illumination optical element; and
a second optical fiber in communication with the collection optical element;
wherein the first optical fiber is at least substantially optically isolated from the collection optical element and the second optical fiber is at least substantially optically isolated from the illumination optical element.

17. The ablation catheter of claim 1,
wherein the illumination optical element includes an external illumination annular surface oriented at an angle relative to the longitudinal axis but having a directional component along the longitudinal axis toward the collection optical element; and
wherein the collection optical element includes an external collection annular surface having a convex profile, the convex profile including a rearward portion oriented at an angle relative to the longitudinal axis but having a directional component along the longitudinal axis toward the illumination optical element and a forward portion oriented at an angle relative to the longitudinal axis but having a directional component along the longitudinal axis toward the distal light transmission opening.

18. The ablation catheter of claim 1, further comprising a light transmission element, and wherein the light transmission element has a hollow interior, the ablation catheter further comprising:
at least one irrigation fluid channel coupled with the hollow interior of the light transmission element and being in thermal communication with the distal portion of the catheter body.

19. The ablation catheter of claim 1,
wherein at least a portion of one of the illumination optical element or the collection optical element is liquid-permeable.

20. The ablation catheter of claim 1,
wherein the illumination optical element is annular and the collection optical element is annular, and the illumination optical element is axially spaced from the collection optical element;
wherein the illumination optical element is coupled to a light source to emit light sideways to the targeted tissue region; and
wherein the collection optical element is configured to receive sideways the returned, backscattered or newly excited light from the targeted tissue region in response to the light emitted sideways from the illumination optical element.

21. The ablation catheter of claim 1,
wherein one element of the illumination optical element or the collection optical element is annular and oriented sideways at an angle relative to the longitudinal axis but having a directional component along the longitudinal axis toward the distal end, and the other element of the illumination optical element or the collection optical element is oriented in a forward direction toward the distal end and disposed distally with respect to the one element.

22. An ablation catheter comprising:
an elongated catheter body extending longitudinally between a proximal end and a distal end along a longitudinal axis;

at least one ablation element disposed in a distal portion which is adjacent the distal end of the catheter body to ablate a targeted tissue region outside the catheter body;

an illumination or excitation optical element disposed in the distal portion, the illumination optical element being light-transmissive to emit light from the illumination optical element to the targeted tissue region;

a collection optical element disposed in the distal portion, the collection optical element being light-transmissive to collect one or more of returned, backscattered or newly excited light from the targeted tissue region in response to the light emitted from the illumination or excitation optical element to the targeted tissue region; and a barrier disposed between the illumination or excitation optical element and the collection optical element to substantially prevent light from traveling between the illumination optical element and the collection optical element along a path within the distal portion, wherein the illumination or excitation optical element and the collection optical element are axially spaced from one another and axially optically isolated from one another within the distal portion by the barrier.

23. The ablation catheter of claim 22, wherein the at least one ablation element is adjacent at least one of the illumination optical element or the collection optical element.

24. The ablation catheter of claim 23, wherein the at least one ablation element comprises a metallic film which at least partially covers at least one of the illumination optical element or the collection optical element, the metallic film being substantially transparent optically and electrically conductive.

25. The ablation catheter of claim 24, wherein the at least one ablation element further comprises a metal-containing block disposed between the illumination optical element and the collection optical element, the metal-containing block being electrically coupled to the metallic film.

26. The ablation catheter of claim 23, wherein the at least one ablation element comprises a metallic shell which at least partially covers at least one of the illumination optical element or the collection optical element; and wherein the metallic shell includes a plurality of first openings through which to emit light from the illumination optical element to the targeted tissue region and a plurality of second openings through which to collect, by the collection optical element, light from the targeted tissue region in response to the light emitted from the illumination optical element to the targeted tissue region.

27. The ablation catheter of claim 26, wherein the at least one ablation element comprises a metallic shell which at least partially covers the illumination optical element but not the collection optical element.

28. The ablation catheter of claim 22, wherein the at least one ablation element comprises a metal-containing block disposed between the illumination optical element and the collection optical element.

* * * * *